United States Patent
Theriot et al.

(10) Patent No.: US 10,682,508 B1
(45) Date of Patent: *Jun. 16, 2020

(54) ELECTRICALLY STIMULATED CBD INFUSED ANESTHETIC PATCH SYSTEM

(71) Applicants: Trevor Theriot, Las Vegas, NV (US); Quanqin Dai, Diamond Bar, CA (US); Mark Julian, Newport Richie, FL (US); Joseph Horton, Newport Beach, CA (US); John Lasso, Lagina Hills, CA (US)

(72) Inventors: Trevor Theriot, Las Vegas, NV (US); Quanqin Dai, Diamond Bar, CA (US); Mark Julian, Newport Richie, FL (US); Joseph Horton, Newport Beach, CA (US); John Lasso, Lagina Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/375,816

(22) Filed: Apr. 4, 2019

(51) Int. Cl.
| | |
|---|---|
| A61N 1/30 | (2006.01) |
| A61N 1/04 | (2006.01) |
| A61B 5/00 | (2006.01) |
| A61N 1/36 | (2006.01) |
| A61K 31/352 | (2006.01) |
| A61K 31/167 | (2006.01) |
| A61K 9/70 | (2006.01) |
| A61N 1/32 | (2006.01) |
| A61K 9/00 | (2006.01) |

(52) U.S. Cl.
CPC .......... *A61N 1/0448* (2013.01); *A61B 5/6833* (2013.01); *A61K 31/352* (2013.01); *A61N 1/0456* (2013.01); *A61N 1/36021* (2013.01); *A61K 9/0014* (2013.01); *A61K 9/7038* (2013.01); *A61K 31/167* (2013.01); *A61N 1/303* (2013.01); *A61N 1/325* (2013.01)

(58) Field of Classification Search
CPC ........ A61N 1/303; A61N 1/30; A61N 1/0456; A61B 5/0408; A61B 5/6833
See application file for complete search history.

(56) References Cited

U.S. PATENT DOCUMENTS

2004/0138712 A1* 7/2004 Tamarkin ............. A61N 1/0428 607/3
2019/0078168 A1* 3/2019 Sayre ........................ C12P 7/42

* cited by examiner

*Primary Examiner* — Alyssa M Alter
(74) *Attorney, Agent, or Firm* — Ruben Alcoba, Esq.

(57) ABSTRACT

An electrically stimulated CBD infused anesthetic patch system that is placed on a human's skin that is used to relieve pain. The electrically stimulated CBD infused anesthetic patch system comprises of a transdermal patch that has electrodes that receive an electric current from a TENS device. The transdermal patch is impregnated with a solution that has at least one analgesic that is selected from the group consisting of Menthol, CBD, Lidocaine or Capsaicin. The solution shall also include inactive ingredients.

2 Claims, 3 Drawing Sheets

ELECTRICALLY STIMULATED CBD INFUSED ANESTHETIC PATCH SYSTEM

CROSS REFERENCE

Figure 1:
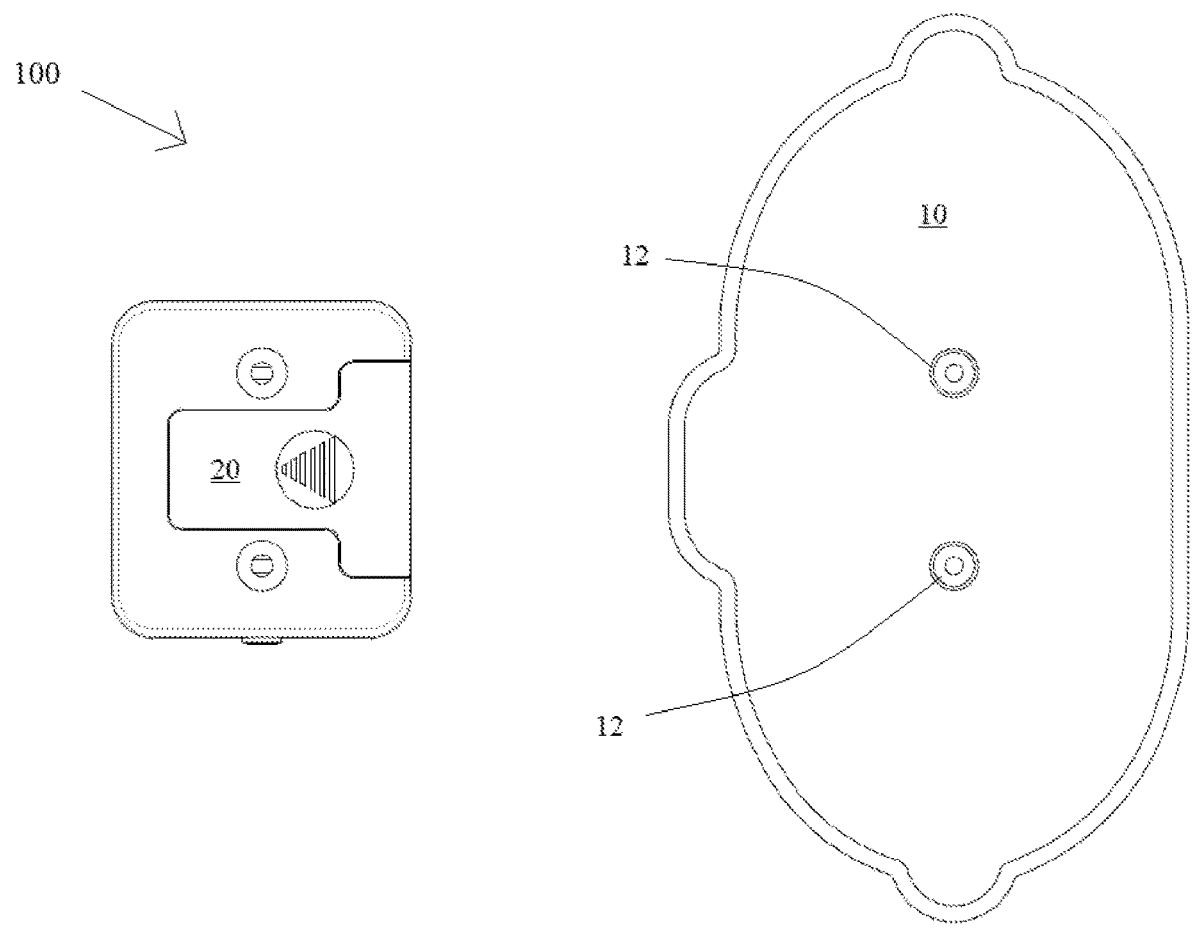

This application is a continuation-in-part of application Ser. No. 15/832,932, filed 6 Dec. 2017, titled Conductive Pad for pain relieving and muscle training.

BACKGROUND

The present invention is directed to an electrically stimulated CBD infused anesthetic patch system that is placed on a human's skin.

Transcutaneous electrical nerve stimulation (TENS) is an inexpensive nonpharmacological intervention used in the treatment of acute and chronic pain conditions.[1] These small battery-powered devices deliver alternating current via cutaneous electrodes positioned near the painful area.[2]

[1] Available at https://www.ncbi.nlm.nih.gov/pmc/articles/PMC4186747/, Using TENS for pain control: the state of the evidence, Carol G T Vance, Dana L Dailey, Barbara A Rakel & Kathleen A Sluka, Published Online:23 Jun. 2014https://doi.org/10.2217/pmt.14.13, seen on Apr. 2, 2019.
[2] id.

A transdermal patch is a medicated adhesive patch that is placed on the skin to deliver a specific dose of medication through the skin and into the bloodstream.[3]

[3] Available at https://en.wikpedia.org/wiki/Transdermal_patch, Wikipedia, Transdermal Patch, seen on Apr. 2, 2019.

Cannabidiol (hereinafter "CBD") is a phytocannabinoid derived from *Cannabis* species, which is devoid of psychoactive activity, with analgesic, anti-inflammatory, antineoplastic and chemopreventive activities.[4]

[4] Available at https://pubchem.ncbi.nlm.nih.gov/compound/cannabidiol, National Center for Biotechnology Information. PubChem Database. Cannabidiol, CID=644019, https://pubchem.ncbi.nlm.nih.gov/compound/644019 (accessed on Apr. 3, 2019)

Capsaicin is a neuropeptide releasing agent selective for primary sensory peripheral neurons. Used topically, capsaicin aids in controlling peripheral nerve pain.[5]

[5] Available at https.//pubchem.ncbi.nlm.nih.gov/compound/Capsaicin, National Center for Biotechnology Information. PubChem Database. Capsaicin, CID=1548943, https://pubchem.ncbi.nlm.nih.gov/compound/1548943 (accessed on Apr. 3, 2019).

Lidocaine patches are used to relieve the pain of postherpetic neuralgia (PHN; the burning, stabbing pains, or aches that may last for months or years after a shingles infection).[6] Lidocaine is a local anesthetic.[7] It stops nerves from sending pain signals to the brain.[8]

[6] Available at https://medlineplus.gov/druginfo/meds/a603026.html, US National Library of Medicine, Lidocaine Transdermal Patch, seen on Apr. 2, 2019.
[7] id.
[8] id.

Topical menthol gels are classified "topical analgesics" and are claimed to relieve minor aches and pains of the musculoskeletal system.[9] Menthol has been reported to be effective in relieving pain with mild to moderate muscle strains.[10]

[9] Available at https://www.ncbi.nlm.nih.gov/pmc/articles/PMC4178917/, Sundstrup E, Jakobsen M D, Brandt M, et al. Acute effect of topical menthol on chronic pain in slaughterhouse workers with carpal tunnel syndrome: triple-blind, randomized placebo-controlled trial. Rehabil Res Pract. 2014; 2014:310913. doi:10.1155/2014/310913.
[10] Available at Higashi Y, Kiuchi T, Furuta K, Efficacy and safety profile of a topical methyl salicylate and menthol patch in adult patients with mild to moderate muscle strain: a randomized, double-blind, parallel-group, placebo-controlled, multicenter study. Clinical Therapy 32. 2010; (1):34-43.

The present invention is comprises of an impregnated analgesic transdermal patch and an electrical stimulator that applies an electric current to the patch when the patch is placed on a human. When the patch is adhered to the skin of a user and the electric current is applied, the user's skin is stimulated by the current and the user's blood circulation is increased, the increased blood circulation allows the skin to absorb more of the analgesic impregnated on the transdermal patch by a factor of 12.

For the foregoing reason there is a need for an electrically stimulated CBD infused anesthetic patch system that is placed on a human's skin that is used to relieve pain.

SUMMARY

The present invention describes an electrically stimulated CBD infused anesthetic patch system that is placed on a human's skin that is used to relieve pain.

The electrically stimulated CBD infused anesthetic patch system comprises of a transdermal patch that has electrodes that receive an electric current from a TENS device. The transdermal patch is impregnated with a solution that has at least one analgesic that is selected from the group consisting of Menthol, CBD, Lidocaine or Capsaicin. The solution shall also include inactive ingredients.

An object of the present invention is to provide an electrically stimulated CBD infused anesthetic patch system that will maximize the release of a pain reliever onto a user's skin.

Another object of the present invention is to provide an electrically stimulated CBD infused anesthetic patch system that will treat pain.

Yet another object of the present invention is to provide an electrically stimulated CBD infused anesthetic patch system that will increase blood flow in treated areas.

Still another object of the present invention is to provide an electrically stimulated CBD infused anesthetic patch system that will relieve pain associated with arthritis.

DRAWINGS

Figure 2:
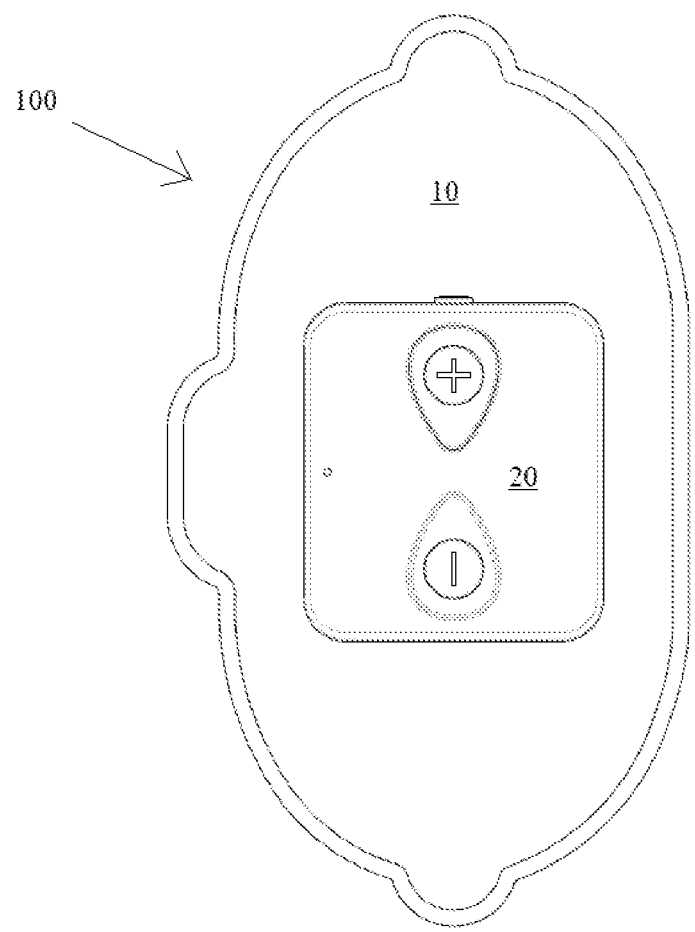
Figure 3:
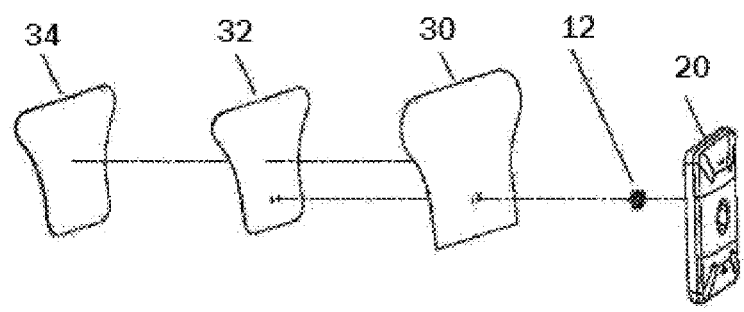

These and other features, aspects, and advantages of the present invention will become better understood with regards to the following description, appended claims, and drawings where:

FIG. 1 a photograph that shows an electrically stimulated CBD infused anesthetic patch system that is placed on a human's skin that is used to relieve pain;

FIG. 2 a photograph that shows the TENS device connected to the anesthetic patch of the present invention: and FIG. 3 is a view of an embodiment of the present invention.

DETAILED DESCRIPTION

As seen in FIGS. 1-3, the present invention describes an electrically stimulated CBD infused anesthetic patch system 100 that is placed on a human's skin that is used to relieve pain. The system 100 comprises a transdermal patch 10 that has at least on electrode 12, wherein the patch is impregnated with a solution that comprises of at least one analgesic. And, a controlled electrical current generating device 20 that delivers an electric current to the transdermal patch 10 after the patch 10 is placed on a user. In embodiments of the present invention, the transdermal patch 10 comprises of a carrier 30 that has at least one electrode 12, at least one conductive electrode sheet 32 that is attached to the carrier 30, and the solution is a conductive gel 34 that is placed on the electrode sheet 32. The controlled electrical current generating device 20 can be either a TENS device, an interferential device or an EMS device.

The at least one analgesic is selected from the group consisting of Menthol, CBD, Lidocaine or Capsaicin. In a preferred embodiment, the analgesic comprises of CBD in the range from about 0.001 percent to about 20.000 percent of the solution and Lidocaine in the range from about 0.001 percent to about 10.000 percent of the solution.

In another embodiment of the present invention, the analgesic further comprises of Menthol in the range from about 0.010 percent to about 20.000 percent of the solution.

In still another embodiment of the present invention, the analgesic shall further comprise of Capsaicin in the range from about 0.001 percent to about 8.000 percent of the solution.

The solution of the present invention shall comprise of inactive compounds. In a preferred embodiment, the inactive compounds shall be Water, Glycerin, Propylene Glycol, PVP, Sodium Polyacrylate, Methylparaben, Propylparaben, Aluminum Glycinate, Kaolin, Polyacrylic Acid, Polysorbate 80, Tartaric Acid, and/or Titanium Dioxide. Depending on the embodiment of the present invention, the inactive compounds shall be added to the solution until a one hundred percent measurement is reached.

The system is used by placing the patch on a user, connecting the patch to the TENS device, powering the TENS device to deliver a charge. The patches can remain on a user's skin for a period between eight to twelve hours. An Electrical Muscle Stimulation device can also be used to provide the electric current to the transdermal patch.

An advantage of the present invention is that it provides an electrically stimulated CBD infused anesthetic patch system that maximizes the release of a pain reliever onto a user's skin.

Another advantage of the present invention is that it provides an electrically stimulated CBD infused anesthetic patch system that treats pain.

Yet another advantage of the present invention is that it provides an electrically stimulated CBD infused anesthetic patch system that increases blood flow in treated areas.

Still another object of the present invention is that it provides an electrically stimulated CBD infused anesthetic patch system that relieves pain associated with arthritis.

While the inventor's above description contains many specificities, these should not be construed as limitations on the scope, but rather as an exemplification of several preferred embodiments thereof. Accordingly, the scope should not be determined by the embodiments illustrated, but by the appended claims and their legal equivalents.

What is claimed is:

1. An electrically stimulated CBD infused anesthetic patch system that is placed on a human's skin that is used to relieve pain, the system comprises:
   a transdermal patch that has at least on electrode, wherein the patch is impregnated with a solution that comprises:
      a CBD in the range from about 0.001 percent to about 20.000 percent of the solution;
      a Lidocaine in the range from about 0.001 percent to about 10.000 percent of the solution;
      a Menthol in the range from about 0.010 percent to about 20.000 percent of the solution; and
      a Capsaicin in the range from about 0.001 percent to about 8.000 percent of the solution; and
   a controlled electrical current generating device that is either a TENS device, an interferential device or an EMS device that delivers an electric current to the transdermal patch after the patch is placed on a user, and wherein the transdermal patch comprises:
   a carrier that has at least one electrode;
   at least one conductive electrode sheet that is attached to the carrier, and wherein the solution is a conductive gel that is placed on the electrode sheet.

2. The electrically stimulated CBD infused anesthetic patch system that is placed on a human's skin that is used to relieve pain of claim 1, the solution further comprises of inactive ingredients.

* * * * *